United States Patent [19]

Taketani et al.

[11] Patent Number: 5,196,147
[45] Date of Patent: Mar. 23, 1993

[54] ORGANIC NONLINEAR OPTICAL SUBSTANCE

[75] Inventors: Yutaka Taketani; Hiroshi Matsuzawa, both of Hino; Kaoru Iwata, Hachioji, all of Japan

[73] Assignee: Teijin Limited, Osaka, Japan

[21] Appl. No.: 329,746

[22] Filed: Mar. 28, 1989

[30] Foreign Application Priority Data

| Mar. 28, 1988 | [JP] | Japan | 63-72080 |
|---|---|---|---|
| May 17, 1988 | [JP] | Japan | 63-118327 |
| May 30, 1988 | [JP] | Japan | 63-130090 |
| Sep. 8, 1988 | [JP] | Japan | 63-223592 |
| Sep. 8, 1988 | [JP] | Japan | 63-223593 |
| Sep. 12, 1988 | [JP] | Japan | 63-226491 |
| Sep. 13, 1988 | [JP] | Japan | 63-227428 |
| Nov. 15, 1988 | [JP] | Japan | 63-286902 |
| Nov. 15, 1988 | [JP] | Japan | 63-286903 |
| Nov. 17, 1988 | [JP] | Japan | 63-288978 |
| Nov. 17, 1988 | [JP] | Japan | 63-288979 |
| Dec. 26, 1988 | [JP] | Japan | 63-326099 |

[51] Int. Cl.$^5$ .................. F21V 9/04; F21V 9/00; G02B 6/00
[52] U.S. Cl. .................. 252/589; 252/582; 252/587; 359/328; 558/401; 558/404; 558/408
[58] Field of Search .................. 252/582, 587, 589; 558/401, 404, 408; 359/326, 328, 361; 548/541, 543, 544, 546, 547, 551, 561; 549/62, 63, 68, 74, 76, 478, 480, 481, 496, 505, 506

[56] References Cited

U.S. PATENT DOCUMENTS

| 3,174,937 | 3/1965 | Strobel et al. | 252/589 |
| 3,462,475 | 8/1969 | Strobel et al. | 252/589 |
| 3,523,953 | 8/1970 | Strobel et al. | 252/589 |
| 3,546,270 | 12/1970 | Kirchmayr et al. | 252/589 |
| 3,706,700 | 12/1972 | Kirchmayr et al. | 252/589 |
| 4,794,045 | 12/1988 | Robin et al. | 252/589 |

FOREIGN PATENT DOCUMENTS 62-203136  7/1987  Japan .

OTHER PUBLICATIONS

Chemla & Zyss, Nonlinear Optical Properties of Organic Molecules and Crystals, vol. 1, pp. 255-259, 271-272, 282-283 and 289 (1987).

Primary Examiner—Robert L. Stoll
Assistant Examiner—Philip Tucker
Attorney, Agent, or Firm—Sughrue, Mion, Zinn, Macpeak & Seas

[57] ABSTRACT

An organic nonlinear optical substance having the formula (I):

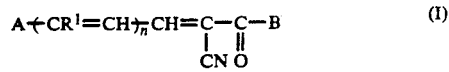

wherein
$R^1$ represents —H or —$CH_3$;
n is 0, 1, or 2;
A represents $Z^1$—Ar,

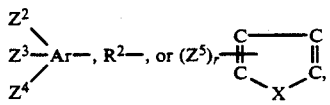

wherein Ar represents a 6-14 membered aromatic group including a heterocyclic ring or biphenylene type ring; $Z^1$ represents H—, $R^5R^6N$—, $R^7O$—, $R^8S$—, NC—, $R^9OCO$—, $R^{10}COO$—, $O_2N$—, $R^{11}R^{12}NOC$, $R^{13}CO(R^{14})N$—, or $R^{15}$—; $Z^2$, $Z^3$, and $Z^4$ independently represent H—, a $C_1$-$C_8$ alkyl—, $R^{16}O$—, $R^{17}R^{18}N$, $R^{19}S$—, $O_2N$—, or two $R^{16}$ being, in combination, $R^{20}CH<$; $R^2$ represents H— or a $C_1$-$C_{12}$ alkyl; $R^5$ to $R^{20}$ independently represent H—, or a $C_1$-$C_{10}$ hydrocarbon residue; $Z^5$ independently represents H—, a $C_1$-$C_8$ saturated hydrocarbon residue, $O_2N$—, $R^{21}O$—, $R^{22}S$—, NC—, or $R^{23}R^{24}N$— wherein $R^{21}$ to $R^{24}$ independently represent H or a $C_1$-$C_8$ saturated hydrocarbon residue; X represents —S—, —O—, or >$NR^{28}$; r is 0 or an integer of 1 to 3; and $R^{28}$ represents H or a hydrocarbon group having 1 to 8 carbon atoms;
B represents —OH.Amine* where Amine* represents an optically active amine; —$OR^3$ where $R^3$ represents a $C_{12}$-$C_{25}$ linear hydrocarbon residue; —$NR^4Y$ where $R^4$ represents —H or a single bond; Y represents —$CH_2)_p$ $CQ^1Q^2Q^3$ where p is 0 or 1; $Q^1$, $Q^2$, and $Q^3$ are different and represent —H, a $C_1$-$C_5$ alkyl, phenyl, naphthyl, —OH, —$CH_2OH$, —$COOR^{25}$, —$CNR^{26}R^{27}$, a residue of an α-amino acid from which an amino group is removed, where $R^{25}$ to $R^{27}$ independently represent —H or —$C_1$-$C_8$ hydrocarbon residue; or —$CQ^4Q^5Q^6$ where $Q^4$, $Q^5$ and $Q^6$ are different and $Q^4$ and $Q^5$ are as defined for $Q^1$, $Q^2$ and $Q^3$ and $Q^6$ represent —$(CH_2)_q$— of which one bond is linked to the bond of $R^4$ where q is an integer of 1 to 4.

11 Claims, No Drawings

ORGANIC NONLINEAR OPTICAL SUBSTANCE

BACKGROUND OF THE INVENTION

1. Field of the Invention

The present invention relates to a novel nonlinear optical material having an increased second harmonic generating ability and usable for an optical switch, an optical memory in an optical data/information processing or optical communication system, or an optical bistable element to be used in optical signal operation. Further, it pertains to a novel nonlinear optical crystalline material containing a salt obtained by the reaction of a conjugated aromatic carboxylic acid compound with an optically active amine.

2. Description of the Related Art

The nonlinear optical effect refers to, for example, a secondary or higher effect of the magnitude of an applied electric field exhibited by the relationship of an electric polarizing response of a substance, which is only primarily proportional to the magnitude of the applied electric field, when, for example, a strong photoelectric field such as a laser beam is applied to the substance.

A secondary nonlinear optical effect may include a second harmonic generation of converting the wavelength of an incident light to a ½ wavelength, a parametric oscillation which converts a light with one kind of wavelength into a light with two kinds of wavelengths, and a secondary light mixing which on the contrary generates a light with one kind of wavelength from a light with two kinds of wavelengths. Due to these various characteristics, materials having a nonlinear optical effect will be for use as an optical switch, optical memory in optical data/information processing, or such elements as optical bistable element, optical switch, etc. to be used in optical signal operations.

Generally speaking, in this field of the art, inorganic materials, primarily $LiNbO_3$, have been studied and investigated, but inorganic materials had a drawback such that great difficulty is encountered in forming a desired optical element, because of such shortcomings as their performance indices which are not so great, small response speed, no good form workability, great hygroscopity, low stability, etc.

In recent years, in contrast to these inorganic materials, researchers are becoming more interested in application of organic materials. This is because the response of organic materials is based primarily on the electron polarization, whereby the nonlinear effect is great, and also the response speed is great, as confirmed and reported in the art. For example, a large number of studies are reported in the ACS Symposium Series Vol. 233, 1983). The secondary nonlinear optical characteristics to be dealt with in the present invention, which is a third rank tensor, cannot be evoked if a symmetric center exists in the molecule or the crystal. For this reason, in the case of organic materials, even when they may have a structure exhibiting an excellent nonlinear effect at molecular level, they must be formed into crystals or solid state for using the second harmonic generation as the practical mode. However, at such stage of solidification, an inversion symmetrical structure will be frequently formed preferentially, whereby there has been involved the problem that a nonlinear optical effect as an optical element can not be exhibited.

SUMMARY OF THE INVENTION

Accordingly, an object of the present invention is to solve the above-mentioned problems of the prior art and to provide an organic crystalline compound for various nonlinear optical elements, and having an increased second harmonic generating ability, a high molecular polarizing ability, and having no inversion symmetry.

Another object of the present invention is to provide an organic crystalline compound having excellent second harmonic generating ability required for a material for forming various optical signal processing elements.

Other objects and advantages of the present invention will be apparent from the following description.

In accordance with the present invention, there is provided an organic nonlinear optical substance having the formula (I):

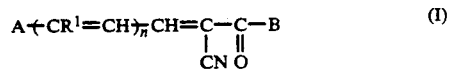

wherein $R^1$ represents —H or —$CH_3$;
n is 0, 1, or 2;
A represents $Z^1$—Ar,

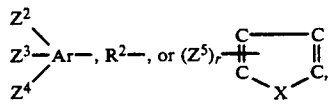

wherein Ar represents a 6–14 membered aromatic group including a heterocyclic ring or biphenylene type ring; $Z^1$ represents H—, $R^5R^6N$—, $R^7O$—, NC—, $R^9OCO$—, $R^{10}COO$—, $O_2N$—, $R^{11}R^{12}NOC$—, $R^{13}CO(R^{14})N$—, or $R^{15}$—; $Z^2$; $Z^3$, and $Z^4$ independently represent H—, a $C_1$-$C_8$ alkyl-, $R^{16}O$—$R^{17}R^{18}N$—, $R^{19}S$—$O_2N$—, or two $R^{16}$ being, in combination, $R^{20}CH>$; $R^2$ represents H— or a $C_1$-$C_{12}$ alkyl; $R^5$ to $R^{20}$ independently represent H—, or a $C_1$-$C_{10}$ hydrocarbon residue; $Z^5$ independently represents H—, a $C_1$-$C_8$ saturated hydrocarbon residue, $O_2N$—, $R^{21}O$—, $R^{22}S$—, NC—, or $R^{23}R^{24}N$—, wherein $R^{21}$ to $R^{24}$ independently represent H or a $C_1$-$C_8$ saturated by hydrocarbon residue; X represents —S—, —O—, or $NR^{28}$; r is 0 or an integer of 1 to 3; and represents H or a hydrocarbon group having 1 to 8 carbon atoms;

B represents —OH.Amine* where Amine* represents an optically active amine; —$NR^4Y$ where $R^4$ represents —H or a single bond; Y represents $(CH_2)_p$ $CQ^1Q^2Q^3$ where p is 0 or 1; $Q^1$, $Q^2$, and $Q^3$ are different and represent —H, a $C_1$-$C_5$ alkyl, phenyl, naphthyl, —OH, —$CH_2OH$, —$COOR^{25}$, —$CNR^{26}R^{27}$, a residue of an α-amino acid from which an amino group is removed, where $R^{25}$ to $R^{27}$ independently represent —H or —$C_1$-$C_8$ hydrocarbon residue, or —$CQ^4Q^5Q^6$ where $Q^4$, $Q^5$ and $Q^6$ are different and $Q^4$ and $Q^5$ are as defined for $Q^1$, $Q^2$ and $Q^3$ and $Q^6$ represents —$(CH_2)_q$— of which one bond is linked to the bond of $R^4$ where q is an integer of 1 to 4.

DESCRIPTION OF THE PREFERRED EMBODIMENTS

Generally speaking, the second harmonic generating ability is greater in a longer conjugated system, in which polarization within the molecular is greater and also contribution of the polarization is greater, but with elongation of the conjugated length, the absorption maximum is shifted toward the longer wavelength side, whereby correspondence to a ½ wavelength of the incident light may occur. In this case, optical damage may occur which absorbs the second harmonic generated and changes the refractive index, chemical denaturation, or combustion by an absorption of heat energy. Accordingly, it is frequently disadvantageous to simply elongate the conjugated length. For example, a compound increased in molecular polarization due to an insertion of a carboxyl group represented by the formula (I) shown below, a group hewing a high electron attractability such as a cyano group, and further various substituents into benzene nucleus may be expected to have large nonlinearily as the result of shifting effect of electron arrangement within the ring, but practically has a structure with an inversion asymmetry center due to a large molecular polarization, whereby frequently a generation of the second harmonic can not be observed. Generally speaking, it is a difficult technique to control the crystalline structure, particularly to form a crystal form which will collapse the symmetry center. Accordingly, while an excellent nonlinear susceptibility may be expected to be possessed at molecular level, most examples prove to be no longer effective as the second harmonic generating material. As the result of intensive studies, as shown in the present invention, by use of an optically active amine as the basic substance to introduce its optically active asymmetric structure thereof as the carboxylic acid salt, and consequently a structure without an inversion asymmetry center can be prepared to accomplish the present invention. As a consequence, the great nonlinear susceptibility at molecular level can be exhibited as such as the crystal structure, and this may be considered to contribute greatly to applications in this field of the art.

To enhance the nonlinear optical effect, it is necessary to have a large dipole within one molecular structure, and for this purpose, the general formula has cyano group, carboxyl group permitted to exist on the same carbon atom. Also, for the molecular polarizations to interfere with each other, it is desirable that a conjugated system exists, but an elongation of the conjugated length will result in an elongation of the absorption maximum to the longer wavelength side, whereby there is the possibility that the damage may be formed due to the incident light wavelength or the second harmonic wavelength. For this reason, the conjugated length should not be too long.

From the above-mentioned standpoints, it has been found that α-cyanoacrylic acid derivatives having a conjugated group are effective as an acid moiety having a conjugated system. Furthermore, the compounds having the formula (I) including the optically active amine salts or amides are effective for providing asymmetry center, as mentioned above.

According to a first embodiment of the present invention, the organic nonlinear optical substance has the general formula (I) wherein $R^1$ represent H, $Z^1$ represents H—, $R^5R^6N$—, $R^7O$—, $R^8S$—, NC—, $R^9OCO$—, $O_2N$—, $R^{10}COO$—, $R^{11}R^{12}NOC$—, $R^{13}CO(R^{14})N$—, or $R^{15}$—, Ar represents an aromatic group having 5 to 14 carbon atoms, and B represents —OH.Amine* wherein Amine* represents an optically active amine selected from the group consisting of 1-(phenyl)ethylamine, 1-(α-naphthy)ethylamine, 1-phenyl-2-methylethylamine, 1-phenyl-2-aminopropane, and brucine.

These amines are strong bases and, therefore, easily react with carboxylic acids to form stable salts in any conventional method.

The optically active amines may be dextrorotatory or levorotatory. Formation of the salt may be carried out by conventional neutralization reaction, which may be in either state of a solution or a solid phase.

For maintaining the purity of the optical activity, it is not preferable to carry out the reaction at too high a temperature, but it is desirable to contrive to inhibit heat generation during salt formation. Salt formation will frequently give a product which differs in solubility to a great extent from the starting material, and therefore existence of salt formation can be easily confirmed and its purification can be also easily done.

The optically active amine salt of the carboxylic acid thus obtained assumes a crystalline state, having excellent moldability, and can be formed into various elements under the crystalline form as such or as a solid solution, which can be then applied to the nonlinear optical application field.

The organic nonlinear optical substances according to the first embodiment of the present invention have an extremely large second harmonic ability. The carboxylic acid moiety of this compound can be preferably derived from the caboxylic acids having the structure (II)

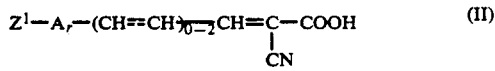

(II)

Examples of such carboxylic acid may include: substituted phenyl 2-cyanopropenoic acid derivatives such as 3-phenyl-2-cyanopropenoic acid, 3-(p-dimethylaminophenyl)-2-cyanopropenoic acid, 3-(p-aminophenyl)-2-cyanopropenoic acid, 3-(p-diethylaminophenyl)-2-cyanopropenoic acid, 3-(p-dipropylaminophenyl)-2-cyanopropenoic acid, 3-(p-dibutylaminophenyl)-2-cyanopropenoic acid, 3-(p-monomethylaminophenyl)-2-cyanopropenoic acid, 3-(p-monoethylaminophenyl)-2-cyanopropenoic acid, and the m- or o- substituted derivatives;

3-(p-methyloxyphenyl)-2-cyanopropenoic acid, 3-(p-ethyloxyphenyl)-2-cyanopropenoic acid, 3-(p-propyloxyphenyl)-2-cyanopropenoic acid, 3-(p-butyloxyphenyl)-2-cyanopropenoic acid, 3-(p-pentyloxyphenyl)-2-cyanopropenoic acid, 3-(p-n-hexyloxyphenyl)-2-cyanopropenoic acid, 3-(p-decanoxyphenyl)-2-cyanopropenoic acid, and the m- or o- substituted derivatives;

3-(p-methylthiophenyl)-2-cyanopropenoic acid, 3-(p-ethylthiophenyl)-2-cyanopropenoic acid, 3-(p-propylthiophenyl)-2-cyanopropenoic acid, 3-(p-butylthiophenyl)-2-cyanopropenoic acid, 3-(p-pentylthiophenyl)-2-cyanopropenoic acid, 3-(p-n-hexylthiophenyl)-2-cyanopropenoic acid, 3-(p-decanethiophenyl)-2-cyanopropenoic acid, and the m- (or o- substituted derivatives;

3-(p-cyanophenyl)-2-cyanopropenoic acid, 3-(m-cyanophenyl)-2-cyanopropenoic acid, 3-(o-cyanophenyl)-2-cyanopropenoic acid, 3-(p-methyloxycarbonylphenyl)-2-cyanopropenoic acid, 3-(p-ethyloxycarbonylphenyl)-2-cyanopropenoic acid, 3-(p-propyloxycarbonylphenyl)-2-cyanopropenoic acid, and the m- or o- substituted derivatives;

3-(p-acetyloxyphenyl)-2-cyanopropenoic acid, 3-(p-propionyloxyphenyl)-2-cyanopropenoic acid, 3-(p-butanoylphenyl)-2-cyanopropenoic acid, and the m- or o- substituted derivatives;

3-(p-nitrophenyl)-2-cyanopropenoic acid, 3-(m-nitrophenyl)-2-cyanopropenoic acid, 3-(o-nitrophenyl)-2-cyanopropenoic acid, 3-(p-dimethylamidophenyl)-2-cyanopropenoic acid, 3-(p-diethylamidophenyl)-2-cyanopropenoic acid, 3-(p-dipropylamidophenyl)-2-cyanopropenoic acid, 3-(p-dibutylamidophenyl)-2-cyanopropenoic acid, and the m- or o- substituted derivatives;

3-(p-acetylaminophenyl)-2-cyanopropenoic acid, 3-(p-propionylaminophenyl)-2-cyanopropenoic acid, and the m- or o- substituted derivatives;

3-(p-methylphenyl)-2-cyanopropenoic acid, 3-(p-ethylphenyl)-2-cyanopropenoic acid, 3-(p-propylphenyl)-2-cyanopropenoic acid, 3-(p-butylphenyl)-2-cyanopropenoic acid, 3-(p-pentylphenyl)-2-cyanopropenoic acid, 3-(p-n-hexylphenyl)-2-cyanopropenoic acid, 3-(p-decanephenyl)-2-cyanopropenoic acid, and the m- or o- substituted derivatives;

Substituted phenyl 2-cyano-2,4-pentadienoic acid derivatives such as:

2-cyano-5-phenyl-2,4-pentadienoic acid, 2-cyano-5-(p-dimethylaminophenyl)-2,4-pentadienoic acid, 2-cyano-5-(p-diethylaminophenyl)-2,4-pentadienoic acid, 2-cyano-5-(p-dipropylaminophenyl)-2,4-pentadienoic acid, 2-cyano-5-(p-dibutylaminophenyl)-2,4-pentadienoic acid, 2-cyano-5-(p-monomethylaminophenyl)-2,4-pentadienoic acid, 2-cyano-5-(p-aminophenyl)-2,4-pentadienoic acid, and the m- or o- substituted derivatives;

2-cyano-5-(p-methyloxyphenyl)-2,4-pentadienoic acid, 2-cyano-5-(p-ethyloxyphenyl)-2,4-pentadienoic acid, 2-cyano-5-(p-propyloxyphenyl)-2,4-pentadienoic acid, 2-cyano-5-(p-butyloxyphenyl)-2,4-pentadienoic acid, and m-, o- substituted derivatives thereof; 2-cyano-5-(p-methylthiophenyl)-2,4-pentadienoic acid, 2-cyano-5-(p-ethylthiophenyl)-2,4-pentadienoic acid, 2-cyano-5-(p-propylthiophenyl)-2,4-pentadienoic acid, 2-cyano-5-(p-butylthiophenyl)-2,4-pentadienoic acid, and m-, o- substituted derivatives thereof;

5-(p-cyanophenyl)-2,4-pentadienoic acid, and m-, o- substituted derivatives thereof;

2-cyano-5-(p-methyloxycarbonylphenyl)-2,4-pentadienoic acid, 2-cyano-5-(p-ethyloxycarbonylphenyl)-2,4-pentadienoic acid, 2-cyano-5-(p-propyloxycarbonylphenyl)-2,4-pentadienoic acid, 2-cyano-5-(p-butyloxycarbonylphenyl)-2,4-pentadienoic acid, and m-, o- substituted derivatives thereof;

2-cyano-5-(p-acetyloxyphenyl)-2,4-pentadienoic acid, 2-cyano-5-(p-propionyloxyphenyl)-2,4-pentadienoic acid, 2-cyano-5-(p-butanoyloxyphenyl)-2,4-pentadienoic acid, and m-, o- substituted derivatives thereof;

2-cyano-5-(p-nitrophenyl)-2,4-pentadienoic acid, and m-, o- substituted derivatives thereof;

2-cyano-5-(p-dimethylamidophenyl)-2,4pentadienoic acid, 2-cyano-5-(p-diethylamidophenyl)-2,4pentadienoic acid, 2-cyano-5-(p-dipropylamidophenyl)-2,4-pentadienoic acid, 2-cyano-5-(p-dibutylamidophenyl)-2,4-pentadienoic acid, 2-cyano-5-(p-monomethylamidophenyl)-2,4-pentadienoic acid, 2-cyano-5-(p-amidophenyl)-2,4-pentadienoic acid, and m-, o- substituted derivatives thereof;

2-cyano-(5-p-acetylaminophenyl)-2,4-pentadienoic acid, 2-cyano-(5-p-propionylaminophenyl)-2,4-pentadienoic acid and m-, o- substituted derivatives thereof;

2-cyano-5-(p-methylphenyl)-2,4-pentadienoic acid, 2-cyano-5-(p-ethylphenyl)-2,4-pentadienoic acid, 2-cyano-5-(p-propylphenyl)-2,4-pentadienoic acid, 2-cyano-5-(p-butylphenyl)-2,4-pentadienoic acid and m-, o- substituted derivatives thereof;

Substituted phenyl 2-cyano-2,4,6-heptatrienoic acid derivatives such as:

2-cyano-7-phenyl-2,4,6-heptatrienoic acid, 2-cyano-7-(p-dimethylaminophenyl)-2,4,6-heptatrienoic acid, 2-cyano-7-(p-diethylaminophenyl)-2,4,6-heptatrienoic acid, 2-cyano-7-(p-dipropylaminophenyl)-2,4,6-heptatrienoic acid, 2-cyano-7-(p-dibutylaminophenyl)-2,4,6-heptatrienoic acid, 2-cyano-7-(p-aminophenyl)-2,4,6-heptatrienoic acid, 2-cyano-7-(p-monomethylaminophenyl)-2,4,6-heptatrienoic acid, and m-, o- substituted derivatives thereof;

2-cyano-7-(p-methyloxyphenyl)-2,4,6-heptatrienoic acid, 2-cyano-7-(p-ethyloxyphenyl)-2,4,6-heptatrienoic acid, 2-cyano-7-(p-propyloxyphenyl)-2,4,6-heptatrienoic acid, 2-cyano-7-(p-butyloxyphenyl)-2,4,6-heptatrienoic acid, and m-, o- substituted derivatives thereof;

2-cyano-7-(p-methylthiophenyl)-2,4,6-heptatrienoic acid, 2-cyano-7-(p-ethylthiophenyl)-2,4,6-heptatrienoic acid, 2-cyano-7-(p-propylthiophenyl)-2,4,6-heptatrienoic acid, 2-cyano-7-(p-butylthiophenyl)-2,4,6-heptatrienoic acid, and m-, o- substituted derivatives thereof;

2-cyano-7-(p-cyanophenyl)-2,4,6-heptatrienoic acid, and m-, o- substituted derivatives thereof;

2-cyano-7-(p-methyloxycarbonylphenyl)-2,4,6-heptatrienoic acid, 2-cyano-7-(p-ethyloxycarbonylphenyl)-2,4,6-heptatrienoic acid, 2-cyano-7-(p-propyloxycarbonylphenyl)-2,4,6-heptatrienoic acid, 2-cyano-7-(p-butyloxycarbonylphenyl)-2,4,6-heptatrienoic acid, and m- or o- substituted derivatives;

2-cyano-7-(p-acetyloxyphenyl)-2,4,6-heptatrienoic acid, 2-cyano-7-(p-propionyloxyphenyl)-2,4,6-heptatrienoic acid, 2-cyano-7-(p-butanoyloxyphenyl)-2,4,6-heptatrienoic acid, and the m- or o- substituted derivatives;

2-cyano-7-(p-nitrophenyl)-2,4,6-heptatrienoic acid, and the m- or o- substituted derivatives;

2-cyano-7-(p-dimethylamidophenyl)-2,4,6-heptatrienoic acid, 2-cyano-7-(p-diethylamidophenyl)-2,4,6-heptatrienoic acid, 2-cyano-7-(p-dipropylamidophenyl)-2,4,6-heptatrienoic acid, 2-cyano-7-(p-dibutylamidophenyl)-2,4,6-heptatrienoic acid, 2-cyano-7-(p-amidophenyl)-2,4,6-heptatrienoic acid, 2-cyano-7-(p-monomethylamidophenyl)-2,4,6-heptatrienoic acid, and the m- or o- substituted derivatives;

2-cyano-7-(p-methylphenyl)-2,4,6-heptatrienoic acid, 2-cyano-7-(p-ethylphenyl)-2,4,6-heptatrienoic acid, 2-cyano-7-(p-propylphenyl)-2,4,6-heptatrienoic acid, 2-cyano-7-(p-butylphenyl)-2,4,6-heptatrienoic acid, and the m- or o- substituted derivatives.

According to a second embodiment of the present invention, the organic nonlinear optical substance has the general formula (I) wherein $R^1$ represents H, $Z^1$ represents H—, $R^5R^6N$—, $R^7O$—, $R^8S$, NC—, $O_2N$—, $R^9OCO$—, $R^{10}COO$—, $R^{11}R^{12}NOC$—, $R^{13}CO(R^{14})N$—, or $R^{15}$—, Ar represents an aromatic group having 6 to 14 carbon atoms, and B represents —OH.Amine* wherein Amine* represents an optically active amine selected from the group consisting of 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino)-1-phenyl-propylamine.

All of the above-mentioned amines have strong basicity and can form readily stable salts with carboxylic acids. Formation of the salt may be carried out by conventional neutralization reaction, which may be in either state of a solution of a solid phase. For maintaining the purity of the optical activity, it is not preferable to carry out the reaction at too high a temperature, but it is desirable to contrive to inhibit heat generation during salt formation. Salt formation will frequently give a product which differs in solubility to a great extent from the starting material, and therefore existence of salt formation can be easily confirmed and its purification can be also easily done.

The optically active amine salt of the carboxylic acid thus obtained assumes a crystalline state, having excellent moldability, and can be formed into various elements under the crystalline form as such or as a solid solution, which can be then applied to the nonlinear optical application field. The carboxylic acid amine salts of this embodiment obtained from the above-mentioned amines especially exhibit excellent damage resistance against laser light.

The carboxylic acid moiety can be derived from the carboxylic acids having the above-mentioned general formula (II).

According to a third embodiment of the present invention, the organic nonlinear optical substance has the general formula (I) wherein $R^1$ represents H, A represents $$\begin{matrix} Z^2 \\ Z^3 - Ar \\ Z^4 \end{matrix}$$

wherein one of $Z^2$, $Z^3$, and $Z^4$ represents H and the remainder independently represents $C_1-C_{10}$ alkyl, $R^{16}O-$, $R^{17}R^{18}N-$, $R^{19}S$, or $O_2N$, Ar represents an aromatic group having 6 to 14 carbon atoms and B represents a residue of an optically active amine selected from the group consisting of 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino-1-phenyl-propylamine.

The caboxylic acid amine salts of this embodiment also exhibit excellent damage resistance against laser light.

The carboxylic acid usable in the present invention, of which molecular polarization occurs as α-cyanocarboxylic acid and in which electrons are localized on the carboxylic acid side, has two substituents which will make such influences effective existing on the aromatic group, and this contributes greatly to exhibition of the nonlinear optical effect. Particularly, the functional groups should be desirably selected mutually so as to give the synergetic effect. From such standpoint, it is desirable to use a carboxylic acid in which a plurality of ether groups, thioether groups, amino groups having the function as the electron donating group are mutually substituted on the aromatic group. Also, depending on the substituted position, electron attracting groups will exhibit a donating function. The above-mentioned carboxylic acids can be represented by the following structure (III).

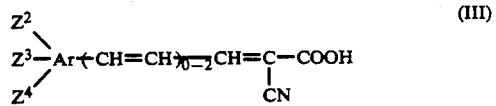

Examples of such carboxylic acid include 3-(3,4-dimethoxyphenyl)-2-cyanopropenoic acid, 3-(3,4-diethoxyphenyl)-2-cyanopropenoic acid, 3-(3,4-dipropyloxyphenyl)-1-cyanopropenoic acid, 3-(2,4-dimethoxyphenyl)-2-cyanopropenoic acid, 3-(2,4-diethoxyphenyl)-2-cyanopropenoic acid, 3-(2,4-dipropyloxyphenyl)-2-cyanopropenoic acid, 3-(3,4-dimethylthiophenyl)-2-cyanopropenoic acid, 3-(3,4-diethylthiophenyl)2-cyanopropenoic acid, 3-(3,4-dipropylthiophenyl)-2-cyanopropenoic acid, 3-(2,4-dimethylthiophenyl)-2-cyanopropenoic acid, 3-(2,4-diethoxyphenyl)-2-cyanopropenoic acid, 3-(2,4-dipropylthiophenyl)-2-cyanopropenoic acid, 3-(3,4-dimethylaminophenyl)-2-cyanopropenoic acid, 3-(3,4-diethylaminophenyl)-2-cyano-1-propenoic acid, 3-(3,4-dipropylaminophenyl)-2-cyanopropenoic acid, 3-(2,4-dimethylphenyl)-2-cyanopropenoic acid, 3-(2,4-diethylaminophenyl)2-cyanopropenoic acid, 3-(2,4-dipropylaminophenyl)-2-cyanopropenoic acid, 3-(3,4-dinitrophenyl)-2-cyanopropenoic acid, 3-(2,4-dinitrophenyl)-2-cyanopropenoic acid, 5-(3,4-dimethoxyphenyl)-2-cyano-2,4-pentadienoic acid, 5-(3,4-diethoxyphenyl)-2-cyano-2,4-pentadienoic acid, 5-(3,4-dipropyloxyphenyl)-2-cyano-2,4-pentadienoic acid, 5-(2,4-(dimethylthiophenyl)-2-cyano-2,4-pentadienoic acid, 5-(2,4-diethylthiophenyl)2-cyano-2,4-pentadienoic acid, 5-(2,4-dipropylthiophenyl)-2-cyano-2,4-pentadienoic acid, 5-(3,4-dimethylthiophenyl)-2-cyano-2,4-pentadienoic acid, 5-(3,4-diethylthiophenyl)-2-cyano-2,4-pentadienoic acid, 5-(3,4-dipropylthiophenyl)-2-cyano-2,4-pentadienoic acid, 5-(2,4-dimethylthiophenyl)-2-cyano-2,4-pentadienoic acid, 5-(2,4-diethylthiophenyl)-2-cyano-2,4-pentadienoic acid, 5-(2,4-dipropylthiophenyl)-2-cyano-2,4-pentadienoic acid, 5-(3,4-dinitrophenyl)-2-cyano-2,4-pentadienoic acid, 5-(2,4-dinitrophenyl)-2-cyano-2,4-pentadienoic acid, 7-(3,4-dimethoxyphenyl)-2-cyano-2,4,6-hexatrienoic acid, 7-(3,4-diethoxyphenyl)-2-cyano-2,4,6-hexatrienoic acid, 7-(3,4-dipropyloxyphenyl)-2-cyano-2,4,6-hexatrienoic acid, 7-(2,4-dimethylthiophenyl)-2-cyano-2,4,6-hexatrienoic acid, 7-(2,4-diethylthiophenyl)-2-cyano-2,4,6-hexatrienoic acid, 7-(2,4-dipropylthiophenyl)-2-cyano-2,4,6-hexatrienoic acid, 7-(3,4-dimethylthiophenyl)-2-cyano-2,4,6-hexatrienoic acid, 7-(3,4-diethylthiophenyl)-2-cyano-2,4,6-hexatrienoic acid, 6-(3,4-dipropylthiophenyl)-2-cyano-2,4,6-hexatrienoic acid, 6-(3,4-dinitrophenyl)-2-cyano-2,4,6-hexatrienoic acid, 7-(2,4-dinitrophenyl)-2-cyano-2,4,6-hexatrienoic acid and the like. The mutual position of the double bonds of these conjugated carboxylic acids should be preferably transform, to obtain a stable structure and also for exhibiting the nonlinear optical effect but is not limited thereto.

The organic substance of the present invention is obtained as a solid with a crystalline structure not having an inversion symmetrical center according to the constitution as described above, and an excellent nonlinear susceptibility at the molecular level is exhibited as such also in the crystalline structure, thus exhibiting an excellent nonlinear optical effect such as a generation of the second harmonic at a high level, and therefore, this substance can be utilized for forming an optical signal processing element.

According to a fourth embodiment of the present invention, the organic nonlinear optical substance has the general formula (I) wherein $R^1$ represents H, A represents

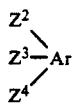

wherein one of $Z^2$, $Z^3$ and $Z^4$ represents H— and the remainder independently represents $C_1$–$C_{10}$ alkyl, $R^{16}O$—, $R^{17}R^{18}N$—, $R^{19}S$, or $O_2N$—, Ar represents an aromatic group having 6 to 14 carbon atoms, and B represents a residue of an optically active amine selected from the group ethyl consisting of 1-(phenyl)ethylamine, 1-(α-naphthyl)ethylamine, 1-phenyl-2-methylethylamine, 1-phenyl-2-aminopropane, and brucine.

The optically active amine salt of the carboxylic acid thus obtained assumes a crystalline state, having excellent moldability, and can be formed into various elements under the crystalline form as such or as a solid solution, which can be then applied to the nonlinear optical application field. The organic nonlinear optical substances according to the first embodiment of the present invention have an extremely large second harmonic ability.

The carboxylic acid moiety of this compound can be preferably derived from the carboxylic acids having the structure (III).

According to a fifth embodiment of the present invention, the organic nonlinear optical substance has the general formula (I) wherein $R^1$ represents H, A represents $Z^1Ar$—, $Z^1$ represents H—, $R^5R^6N$—, $R^7O$—, $R^8S$—, NC—, $O_2N$—, $R^9OCO$—, $R^{10}COO$, $R^{11}R^{12}NOC$—, $R^{13}CO(R^{14})N$—, or $R^{15}$—, Ar represents an aromatic ring having 6 to 14 carbon atoms, and B represents —$NR^4Y$ The moiety —$NR^4Y$ includes, for example, α-chiral substituted primary alkylamines (i.e., p=o) having 4 to 20 carbon atoms such as 1-(methyl)propylamine, 1-(ethyl)propylamine, 1-(methyl)butylamine, 1-(methyl)pentylamine, 1-(phenyl)ethylamine, 1-(α-naphthyl)ethylamine, and 1-(hydroxymethyl)propylamine; β-chiral substituted primary alkylamines (i.e., p=1) having 4 to 20 carbon atoms such as 2-(methyl)butylamine, 2-(methyl)pentylamine, 2-phenylpropylamine, 2-(α-naphthyl)propylamine, and 2-(hydroxybutyl)amine; prolinole; amino acid derivatives having 3 to 20 carbon atoms such as alkyl esters (e.g., methyl esters and ethyl esters) of α-amino acids, α-amino acid amides, α-amino acid anilides, or peptides derived from the same or different α-amino acids. It should be noted, however, that the presence of a carboxyl group as an acid is not preferable from the reaction standpoints. Examples of the typical optically active (either dextrorotatory or levorotatory) amino acids, usable in the present invention are alanine, leucine, isoleucine, ethionine, cysteine, serine, tyrosine, tryptophan, threonine, norvaline, norleucine, valine, histidine, phenylalanine, α-phenylglycine, methionine, and proline; monoamino dicarboxylic acids and carboamides such as aspartic acid, glutamic acid, asparagine, and glutamine; and diaminomonocarboxylic acids such as arginine, lysine, ornithine, canavanine, and hydroxylysine.

The carboxylic acid moiety of this compound can be preferably derived from the carboxylic acids hewing the structure (II).

According to further embodiments of the present invention, the organic nonlinear optical substances have the following general formula (I):

(i) $R^1$ represents H—, A represents $Z^1$—Ar—, $Z^1$ represents $R^5R^6N$—, $R^7O$—, $R^8S$—, NC, $R^9OCO$—, $R^{10}COO$—, $R^{11}R^{12}NOC$, $R^{13}CO(R^{14})N$—, or $R^{15}$, Ar represents an aromatic group having 6 to 14 carbon atoms, and B represents —OH.Amine* wherein Amine* represents an optically active α-amino acid or the derivative thereof, which can include those as mentioned above.

(ii) $R^1$ represents H, A represents

where one of $Z^2$, $Z^3$, and $Z^4$ represents H or substituted $C_1$–$C_8$ alkyl, the remainder of $Z^2$, $Z^3$ and $Z^4$ represents together methylene dioxy group wherein the dioxy groups are bonded to the adjacent positions of Ar, Ar represents an aromatic group having 6 to 14 carbon atoms, and B represents —OH.Amine* wherein Amine* represents an optically active amine selected from the group consisting of 1-(phenyl)-ethylamine, 1-(α-naphthyl)ethylamine, 1-phenyl-2-(methyl)ethylamine, 1-phenyl-2-aminopropane, brucine, 1-butanol, 1-amino-2-propanol, 2-amino-1-propanol, 2-amino-1-(p-nitrophenyl)-1,3-propanediol, 2-dimethylamino-1-phenyl-1-benzyl-1-propanol, 1-(N,N-dimethylamino)-1-phenyl-propylamine, and a residue of an optically active α-amino acid and the derivative thereof; or the above-mentioned $NR^4Y$.

The carboxylic acids forming the organic nonlinear optical substances of this embodiment can be represented by the formula (IV):

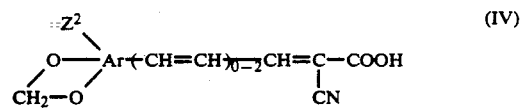

Examples of such carboxylic acids are 3-(3,4-dioxymethylenephenyl)-2-cyanopropenoic acid, 2-cyano-5-(3,4-dioxymethylenphenyl)-2,4-pentadienoic acid, 2-cyano-7-(3,4-dioxymethylenphenyl)-2,4,6-heptatrienoic acid, 3-(3,4-dioxymethylene-6-phenyl)-2-cyanopropenoic acid, 2-cyano-5-(3,4-dioxymethylene-6-propylphenyl)-2,4-pentadienoic acid, 2-cyano-7-(3,4-dioxymethyl-6-propylphenyl)-2,4,6-heptatrienoic acid, and piperonoyl derivatives.

(iii) $R^1$ represents H or $CH_3$, A represents $R^2$ where $R^2$ represents H or an alkyl group having 1 to 12 carbon atoms, and B represents —OH.Amine* wherein Amine* represents an optically active amine selected from the group consisting of 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino)-1-phenyl propylamine.

The carboxylic acids forming the organic nonlinear optical substances of this embodiment can be represented by the formula (V):

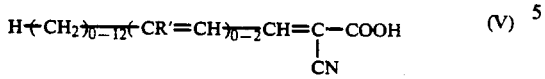
(V)

Examples of such carboxylic acid may include 3-alkyl substituted 2-cyano propionic acid derivatives such as 3-(methyl)-2-cyanopropenoic acid, 3-(n-propyl)-2-cyanopropenoic acid, 3-(n-butyl)-2-cyanopropenoic acid, 3-(n-pentyl)-2-cyanopropenoic acid, 3-(n-hexyl)-2-cyanopropenoic acid;

5-Alkyl substituted 2,4-pentadienoic acid derivatives such as 2-cyano-5-(methyl)-2,4-pentadienoic acid, 2-cyano-5-(n-propyl)-2,4-pentadienoic acid, 2-cyano-5-(n-butyl)-2,4-pentadienoic acid, 2-cyano-5-(n-pentyl)-2,4-pentadienoic acid, 2-cyano-5-(n-hexyl)-2,4-pentadienoic acid, 2-cyano-5-(n-heptyl)-2,4-pentadienoic acid;

5-Alkyl substituted 2,4-pentadienoic acid derivatives such as 2-cyano-5-(methyl)-2,4-hexadienoic acid, 2-cyano-5-(n-propyl)-2,4-hexadienoic acid, 2-cyano-5-(n-butyl)-2,4-hexadienoic acid, 2-cyano-5-(n-pentyl)-2,4-hexadienoic acid, 2-cyano-5-(n-hexyl)-2,4-hexadienoic acid, 2-cyano-5-(n-heptyl)-2,4-hexadienoic acid;

7-Alkyl substituted 2,4,6-heptatrienoic acid derivatives such as 2-cyano-7-(methyl)-2,4,6-heptatrienoic acid, 2-cyano-7-(n-propyl)-2,4,6-heptatrienoic acid, 2-cyano-7-(n-butyl)-2,4,6-heptatrienoic acid, 2-cyano-7-(n-pentyl)-2,4,6-heptatrienoic acid, 2-cyano-7-(n-hexyl)-2,4,6-heptatrienoic acid, 2-cyano-7-(n-heptyl)-2,4,6-heptatrienoic acid;

5-Methyl 7-alkyl substituted 2,4,6-heptatrienoic acid derivatives such as 2-cyano-5-methyl-7-(methyl)-2,4,6-heptatrienoic acid, 2-cyano-5-methyl-7-(n-propyl)-2,4,6-heptatrienoic acid, 2-cyano-5-methyl-7-(n-butyl)-2,4,6-heptatrienoic acid, 2-cyano-5-methyl-7-(n-pentyl)-2,4,6-heptatrienoic acid, 2-cyano-5-methyl-7-(n-hexyl)-2,4,6-heptatrienoic acid, 2-cyano-5-methyl-7-(n-heptyl)-2,4,6-heptatrienoic acid:

7-Alkyl substituted 2,4,6-octatrienoic acid derivatives such as 2-cyano-7-(methyl)-2,4,6-octatrienoic acid, 2-cyano-7-(n-propyl)-2,4,6-octatrienoic acid, 2-cyano-7-(n-butyl)-2,4,6-octatrienoic acid, 2-cyano-7-(n-pentyl)-2,4,6-octatrienoic acid, 2-cyano-7-(n-hexyl)-2,4,6-octatrienoic acid, 2-cyano-7-(n-heptyl)-2,4,6-octatrienoic acid.

(iv) $R^1$ represents H, A represents

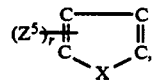

and B represents —OH.Amine* wherein Amine* represents an optically active amine selected from the group consisting of 1-(phenyl)ethylamine, 1-(α-naphthyl)ethylamine, 1-phenyl-2-methylethylamine, 1-phenyl-2-aminopropane, brucine, 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino)-1-phenyl-propylamine; or —$NR^4Y$.

The carboxylic acids forming the organic nonlinear optical substances of this embodiment can be represented by the formula (VI):

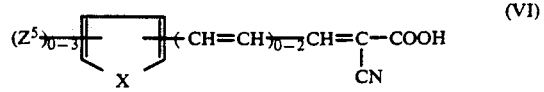
(VI)

Examples of such carboxylic acid may include, for example, 3-(5-membered ring derivatives with hetero atoms) substituted 2-cyanopropenoic acids such as 3-(3-thienyl)-2-cyanopropenoic acid, 3-(2-thienyl)-2-cyanopropenoic acid, 3-(2-pyrrolyl)-2-cyanopropenoic acid, 3-(3-pyrrolyl)-2-cyanopropenoic acid, 3-(2-furyl)-2-cyanopropenoic acid, 3-(3-furyl)-2-cyanopropenoic acid, 3-(2-indolyl)-2-cyanopropenoic acid, 3-(3-indolyl)-2-cyanopropenoic acid, 3-(N-methyl -pyrrolyl)-2-cyanopropenoic acid, 3-(N-methyl 3-pyrrolyl)-2cyanopropenoic acid, 3-(N-ethyl 2-pyrrolyl)-2-cyanopropenoic acid, 3-(N-ethyl 3-pyrrolyl)-2-cyanopropenoic acid, 3-(N-n-butyl 2-pyrrolyl)-2-cyanopropenoic acid, 3-(N-n-butyl 3-pyrrolyl)-2-cyanopropenoic acid, 3-(5-nitro 2-furyl)-2-cyanopropenoic acid, 3-(5-nitro 3-furyl)-2-cyanopropenoic acid, 3-(5-nitro 3-thienyl)-2-cyanopropenoic acid, 3-(5-nitro 2-thienyl)-2-cyanopropenoic acid, 3-(5-chloro 3-indolyl)-2-cyanopropenoic acid; 5-(5-membered ring derivatives with hetero atoms) substituted 2-cyano-2,4-pentadienoic acids such as 2-cyano-5-(3-thienyl)-2,4-pentadienoic acid, 2-cyano-5-(2-thienyl)-2,4-pentadienoic acid, 2-cyano-5-(2-pyrrolyl)-2,4-pentadienoic acid, 2-cyano-5-(3-pyrrolyl)-2,4-pentadienoic acid, 2-cyano-5-(2-furyl)-2,4-pentadienoic acid, 2-cyano-5-(3-furyl)-2,4-pentadienoic acid, 2-cyano-5-(2-indolyl)-2,4-pentadienoic acid, 2-cyano-5-(3-indolyl)-2,4-pentadienoic acid, 2-cyano-5-(N-methyl 2-pyrrolyl)-2,4-pentadienoic acid, 2-cyano-5-(N-methyl 3-pyrrolyl)-2,4-pentadienoic acid, 2-cyano-5-(N-ethyl 2-pyrrolyl)-2,4-pentadienoic acid, 2-cyano-5-(N-ethyl 3-pyrrolyl)-2,4-pentadienoic acid, 2-cyano-5-(N-n-butyl 2-pyrrolyl)-2,4-pentadienoic acid, 2-cyano-5-(N-n-butyl 3-pyrrolyl)-2,4-pentadienoic acid, 2-cyano-5-(5-nitro 2-furyl)-2,4-pentadienoic acid, 2-cyano-5-(5-nitro 3-furyl)-2,4-pentadienoic acid, 2-cyano-5-(5-nitro 2-thienyl)-2,4-pentadienoic acid, 2-cyano-5-(5-nitro 3-thienyl)-2,4-pentadienoic acid, 2-cyano-5-(5-chloro 2-indolyl)-2,4-pentadienoic acid, 5-(5-membered ring derivatives with hetero atoms) substituted 2-cyano-2,4,6-heptatrienoic acids such as 2-cyano-7-(3-thienyl)-2,4,6-heptatrienoic acid, 2-cyano-7-(2-thienyl)-2,4,6-heptatrienoic acid, 2-cyano-7-(2-pyrrolyl)-2,4,6-heptatrienoic acid, 2-cyano-7-(3-pyrrolyl)-2,4,6-heptatrienoic acid, 2-cyano-7-(2-furyl)-2,4,6-heptatrienoic acid, 2-cyano-7-(3-furyl)-2,4,6-heptatrienoic acid, 2-cyano-7-(2-indolyl)-2,4,6-heptatrienoic acid, 2-cyano-7-(3-furyl)-2,4,6-heptatriaenoic acid, 2-cyano-7-(2-indolyl)-2,4,6-heptatrienoic acid, 2-cyano-7-(3-indolyl)-2,4,6-heptatrienoic acid, 2-cyano-7-(N-methyl 2-pyrrolyl)-2,4,6-heptatrienoic acid, 2-cyano-7-(N-methyl 3-pyrrolyl)-2,4,6-heptatrienoic acid, 2-cyano-7-(N-ethyl 2-pyrrolyl)-2,4,6-heptatrienoic acid, 2-cyano-7-(N-ethyl 3-pyrrolyl)-2,4,6-heptatrienoic acid, 2-cyano-7-(N-n-butyl 2-pyrrolyl)-2,4,6-heptatrienoic acid, 2-cyano-7-(N-n-butyl 3-pyrrolyl)-2,4,6-heptatrienoic acid, 2-cyano-7-(5-nitro 2-furyl)-2,4,6-heptatrienoic acid, 2-cyano-7-(5-nitro 3-furyl)-2,4,6-heptatrienoic acid, 2-cyano-7-(5-nitro 2-thienyl)-2,4,6-hexatrienoic acid, 2-cyano-7-(5-nitro 3-thienyl)-2,4,6-heptatrienoic acid, 2-cyano-7-(5-chloro 2-indolyl)-2,4,6-heptatrienoic acid.

EXAMPLE

The present invention will now be further illustrated by, but is by no means limited to, the following Examples.

Synthetic Example 1

Synthesis of 2-cyano-5-4-dimethylaminophenyl)-2,4-pentadienoic acid (1)

To 100 ml of an aqueous solution of 2.55 g of sodium hydroxide 5.97 g of methyl cyanoacetate was added, and further 9.55 g of p-dimethylaminocinnamoyl aldehyde was added under stirring, followed by heating to 85° C. with continuous stirring for 40 hours. After completion of the reaction, 50 ml of 12 N hydrochloric acid was added, and a solid was recovered. The solid was subjected to recrystallization from methanol, repeated twice, to give 6.38 g of the desired product. m.p. 218°-219° C. The elemental analysis of C 68.40%, H 5.88%, N 11.30% coincided well with the calculated values of C 69.36%, H 5.84%, N 11.56%. IR absorption spectrum: presence of CN group at 2216 cm$^{-1}$, COOH group at 1673 cm$^{-1}$, benzene ring and conjugate double bond at 1615, 1586, and 1551 cm$^{-1}$ being recognized. In NMR spectrum, absorption by methyl group was recognized at 3.08 ppm, and AB type absorption based on benzene ring at 6.80 and 7.60 ppm. λmax was found to be 440 nm.

Synthesis Example 2

Synthesis of 2-cyano-3-(4-dimethylaminophenyl)-2-propenoic acid (2)

In 400 ml of an aqueous solution of 13.77 g of sodium hydroxide, 34.80 g of methyl cyanoacetate was dissolved and 34.01 g of p-dimethylamino benzaldehyde was then added under a nitrogen atmosphere, followed by adding 200 ml of ethanol to obtain a uniform solution. Under reflux, the stirring was continued for 51 hours and the reaction mixture was added to 12 N hydrochloric acid to obtain the precipitates. The resultant solid was repeated twice to recrystallize from a methanol/ethanol mixture to obtain 13.51 g of the needles.

NMR spectrum: methyl group at 3.08 ppm, doublet benzene ring at 6.84–6.82 ppm and 7.93–7.95 ppm, and —CH= group at 8.25 ppm Yield: 37%.

m.p.: 226°-228° C.

Elemental analysis: C 66.82%, H 5.56%, N 12.76% (Calc. C 66.14%, H 5.60%, N 12.96%). λmax in ethanol: 399 nm.

Synthesis Example 3

Synthesis of 2-cyano-5-(4-methoxyphenyl)-2,4-pentadienoic acid (3)

The desired compound was prepared in the same manner as in Synthesis Example 1 by using 16.2 g of p-methoxycinnamic aldehyde having a melting point of 45.5° C., which was obtained from p-methoxystyrene and phosphorus trichloride according to a method disclosed in J. Amer. Chem. Soc., 78, 3209 (1956), 4.8 g of sodium hydroxide and 11.3 g of methyl cyanoacetate. The product was recrystallized from ethanol to obtain the needles having a melting point of 240° C. at a yield of 69%.

Elemental analysis: C 68.11%, H 4.81%, N 6.10% (Calc. C 68.10%, H 4.85%, N 6.11%).

NMR spectrum: methyl group at 3.83 ppm, doublet benzene ring around 7.02–7.64 ppm, and —CH=group at 7.09, 7.59 and 8.06 ppm.

λmax in ethanol: 372 nm.

Synthesis Example 4

Synthesis of 2-cyano-3-(3,4-methylenedioxyphenyl)-2-propenoic acid (4)

To an aqueous solution containing 14.20 g of sodium hydroxide and 33.75 g of methyl cyanoacetate, 30.32 g of 3,4-(methylenedioxy)benzaldehyde was added, followed by stirring at 95° C. for 16 hours. After completion of the reaction, an aqueous diluted hydrochloric acid solution was added to obtain a pale yellow solid. The resultant solid was recrystallized from ethanol to obtain a crystal having a melting point of 233° C.

Elemental analysis: C 61.01%, H 3.21%, N 6.37% (Calc. C 60.83%, H 3.26%, N 6.45%).

Infrared spectrum: Absorption by —CN at a wavelength of 2224 cm$^{-1}$, —COO— at 1677 cm$^{-1}$, conjugated system at 1575 cm$^{-1}$ and 1293 cm$^{-1}$.

NMR spectrum: —CH$_2$— at 6.19 ppm(s), —CH= at 8.22 ppm(s), and —H based upon a benzene ring at 7.12, 7.63, and 7.68 ppm.

Synthesis Example 5

Synthesis of 2-cyano-3-(3,4-dimethoxyphenyl)-2-propenoic acid (5)

To 150 ml of an aqueous solution of 9.19 g of sodium hydroxide, 20.50 g of methyl cyanoacetate was added and, under stirring, 25.38 g of 3,4-dimethoxybenzaldehyde was further added, followed by heating at 85° C. for 40 hours under stirring. After completion of the reaction, the reaction mixture was added to 50 ml of 12 N hydrochloric acid to recover the resultant solid. The solid was repeated twice to recrystallize from ethanol to obtain 19.84 g of the desired compound.

M.p.: 206.13° C.

Elemental analysis: C 61.94%, H 4.78%, N 6.04% (Calc. C 61.79%, H 4.76%, N 6.01%).

IR spectrum: Absorption by CN group at 221 cm$^{-1}$, COOH group at 1716 cm$^{-1}$, benzene ring at 1596, 1573, and 1512 cm$^{-1}$ and presence of conjugated double bond.

NMR spectrum: Absorption by methyl group at 3.97–4.01 ppm, ABX type absorption based upon benzene ring at 7.00, 7.55, and 7.88 ppm. λmax in ethanol: 353 nm.

Synthesis Example 6

Synthesis of 2-cyano-3-(2,4-dinitrophenyl)-2-propenoic acid (6)

The desired compound (6) was obtained in the same manner as in Synthesis Example 5, except that 2,4-dinitrobenzaldehyde was used instead of 3,4-dimethoxybenzaldehyde.

M.p.: 210° C.

Elemental analysis: C 46.00%, H 1.98%, N 16.03% (Calc. C 46.53%, H 1.92%, N 15.97%).

Synthesis Example 7

Synthesis of 2-cyano-5-(3,4-dimethoxyphenyl)-2,4-pentadienoic acid (7)

The desired compound (7) was obtained in the same manner as in Synthesis Example 1, except that 2-(3,4-dimethoxyphenyl)-1-formyl 1-propenoic acid obtained from the reaction of 3,4-dimethoxy benzaldehyde and phosphorus trichloride.

M.p.: 190° C.

Elemental analysis: C 64.70%, H 5.15%, N 5.62% (Calc. C 64.85%, H 5.06%, N 5.40%).

Synthesis Examples 8-14

The compounds (8)-(14) shown in Table 1 were synthesized from the corresponding aldehydes and methyl cyanoacetate in the manner described above.

TABLE 1

Synthesis of Aromatic Derivative

| Compound No. | Structure | m.p. (°C.) Elemental analysis (C, H, N)(F: Found/C: Calcd) | $\lambda$max* |
|---|---|---|---|
| 8 | p-NO$_2$—C$_6$H$_4$—CH=C(CN)COOH | 208<br>F 54.91 2.93 12.80/C 55.05 2.75 12.84 | 302 nm |
| 9 | p-CH$_3$—O—C$_6$H$_4$—CH=C(CN)COOH | 229<br>F 65.10 4.64 6.71/C 65.02 4.96 6.89 | 320 nm |
| 10 | H—C$_6$H$_4$—CH=C(CN)COOH | 210<br>F 69.58 4.36 8.03/C 69.35 4.08 8.09 | 295 nm |
| 11 | C$_6$H$_5$—CH=CH—CH=C(CN)COOH | 212<br>F 72.50 4.60 7.01/C 72.34 4.56 7.04 | 320 nm |
| 12 | C$_6$H$_5$—CH=CH—CH=CH—CH=C(CN)COOH | 238<br>F 74.75 4.88 6.35/C 74.64 4.93 6.22 | 360 nm |
| 13 | m-CH$_3$—O—C$_6$H$_4$—CH=C(CN)COOH | 166<br>F 70.69 6.67 12.37/C 71.18 6.88 12.46 | 296 nm |
| 14 | p-C$_{10}$H$_{21}$O—C$_6$H$_4$—CH=C(CN)COOH | 82<br>F 73.55 8.55 4.15/C 73.43 8.53 4.08 | — |

*1: determined in methanol

Synthesis Example 15

Synthesis of trans,trans,trans,2-cyano-7-(n-pentyl)-2,4,6-heptatriene-1-carboxylic acid (15)

To 150 ml of an aqueous solution containing 6.87 g of sodium hydroxide and 16.40 g of methyl cyanoacetate 14.85 g of trans,trans-2,4-decadienal was added, followed by heating at 100° C. for 16 hours under stirring. After completion of the reaction, an excess amount of an aqueous hydrochloric acid solution was added thereto to obtain a viscous solid. The resultant solid was recrystallized from n-hexane to obtain the crystal having a melting point of 98°-102° C.

Elemental analysis: C 70.00%, H 7.75%, N 6.27% (Calc. C 71.19%, H 7.83%, N 6.39%)

IR spectrum: —CN at 2211 cm$^{-1}$, —COO— at 1609 cm$^{-1}$, conjugated system at 1561 cm and 996 cm$^{-1}$.

NMR spectrum: —CH=CH— at 6.25-7.95 ppm, long CH$_2$— and CH$_3$— at 0.85-2.2 ppm, integrated intensity was well coincided.

Synthesis Example 16

Synthesis of trans,trans-2-cyano-5-(n-heptyl)-2,4-pentadienoic acid (16)

The desired compound was synthesized and purified in the same manner as in Synthesis Example 15, except that trans 2-decenal was used as a starting material. Thus crystals were obtained.

Elemental analysis: C 71.20%, H 8.90%, N 6.17% (Calc. C 70.55%, H 8.67%, N 6.33%).

Synthesis Example 17

Synthesis of 2-cyano-3-(2-thienyl)-2-propenoic acid (17)

To 160 ml of an aqueous solution containing 20.97 g of sodium hydroxide and 46.11 g of methyl cyanoacetate, 40.08 g of thiophene 2-carboxyaldehyde was added, followed by heating at 90° C. for 9 hours under stirring. After completion of the reaction, an excess amount of hydrochloric acid was added and the resultant solid was recovered. The solid was recrystallized from ethanol to obtain the needles.

M.p.: 234° C.

Elemental analysis: C 53.63%, H 2.69%, N 7.80%, S 17.70% (Calc.: C 53.61%, H 2.82%, N 7.82%, S 17.89%).

NMR spectrum: proton of thiophen ring at 7.34, 8.02 and 8.17 ppm, proton at p-position at 8.55 ppm.

$\lambda$max in ethanol: 335 nm.

Synthesis Example 18

Synthesis of 2-cyano-3-(3-thienyl)-2-propenoic acid (18)

The desired compound (18) was prepared in the same manner as in Synthesis Example 17, except that thiophene 3-carboxyaldehyde was used instead of thiophene 2-carboxyaldehyde.

M.p.: 211° C.

Elemental analysis: C 53.73%, H 2.71, N 7.73%, S 17.52% (Calc. C 53.61%, H 2.82%, N 7.82%, S 17.89%).

Synthesis Example 19

Synthesis of 2-cyano-3-(2-pyrrolyl)-2-propenoic acid (19)

After 36.93 g of methyl cyanoacetate and 16.94 g of sodium hydroxide were dissolved in 260 ml of water, 23.80 g of pyrrole 2-carboxyaldehyde was added thereto, followed by heating at 95° C. for 30 hours under stirring. Thereafter, hydrochloric acid was added and the resultant solid was recrystallized from a mixed solvent of ethanol/methanol to obtain the crystal having a melting point of 213° C.

Elemental analysis: C 59.34%, H 3.82%, N 17.26% (Calc.: C 59.25%, H 3.73%, N 17.28%).

Synthesis Example 20

Synthesis of 2-cyano-3-(2-furyl)-2-propenoic acid (20)

The desired compound (20) was obtained in the same manner as in Synthesis Example 17, except that furfural was used.

M.p.: 219° C.

Elemental analysis: C 59.02%, H 2.95, N 8.53% (Calc.: C 58.89%, H 3.10%, N 8.59%).

λmax in ethanol: 330 nm.

Synthesis Example 21

Synthesis of 2-cyano-5-(2-furyl)-2,4-pentadienoic acid (21)

The desired compound (21) was prepared in the same manner as in Synthesis Example 17 except that 24.7 g of 3-(2-furyl) acrolein was used.

The melting point of the resultant compound was 220° C. and the structure thereof was confirmed by the elemental analysis value and NMR spectrum. The λmax in ethanol was 368 nm.

Synthesis Example 22

Synthesis of 2-cyano-7-(2-furyl)-2,4,6-heptatriene-1-carboxylic acid (22)

The desired compound (22) was prepared in the same manner as in Synthesis Example 21 except that the aldehyde obtained from the oxidation reaction with phosphorus oxytrichloride mentioned in Synthesis Example 3. The trans structure of the resultant was confirmed by an NMR spectrum.

Synthesis Example 23

Synthesis of 2-cyano-3-(3-indolyl)-2-propenoic acid (23)

The desired compound (23) in the form of a pale yellow flake crystal was obtained at a yield of 33.5% in the same manner as in Synthesis Example 1 by using 21.34 g of indole 3-carboxyaldehyde, 9.47 g of sodium hydroxide and 23.46 g of methyl cyanoacetate.

M.p.: 230° C.

Elemental analysis: C 68.33%, H 3.77%, N 13.29% (Calc.: C 67.92%, H 3.80%, N 13.20%).

λmax in ethanol: 378 nm.

Evaluation method of intensity of second harmonic generation

According to the method as described in S. K. Kurtz et al, Journal of Applied Physics (J. Appl. Phys.), Vol. 39, p. 3798 (published in 1968), the generation of the second harmonic wave was measured for the powder of the compound of the present invention. As the incident ray source, a beam of 1.06μ of Nd:YAG laser (2 W/2 KHz pulse) was employed and irradiated on the powdery sample filled in a glass cell. The incident light was filtered by a filter and the green light generated at an incident angle of 55° from the normal direction was detected to obviate the effect from the strength of the incident light. As the sample for Control, urea powder or m-nitroaniline powder having a particle size of 50 to 90 μm, which was previously powdered, followed by sieving, was employed. Regarding the resistance to a laser beam, the laser beam was irradiated to the sample and the deformation in the appearance was visually observed. Generally, the determination of the principal characteristics was carried out at a non-focus point because the intensity of the laser beam was strong.

Example 1

A 2.39 g amount of the carboxylic acid compound (1) obtained in the Synthesis Example 1 was dissolved in 150 ml of tetrahydrofuran and, to the resultant solution, 1.18 g of L-(−)-1-(phenyl)ethylamine was added under stirring. Momentarily, the precipitate was generated, which was filtered to recover 3.16 g of a reddish orange solid. The solid was recrystallized from ethanol/methanol mixture to obtain 2.16 g of needles. The elemental analysis value of this product was as follows.

C: 72.70% (Calc. *72.09%), H: 6.68% (Calc. *6.95%), N: 11.63% (Calc. *11.56%) *: a 1:1 salt of carboxylic acid (1) and 1-(phenyl)ethylamine.

IR spectrum: carboxylate at 2400–3200 $cm^{-1}$.

In the case of the carboxylic acid (1), the absorbance of the COOH group at 1673 $cm^{-1}$ was shifted to about 1620 $cm^{-1}$ to exhibit the generation of the salt formation.

The NMR spectrum exhibited an absorbance by a methyl group at 2.95 ppm, benzene at 6.74–7.50 ppm, and methyl group of 1-(phenyl)ethylamine at 1.50 ppm. The relative ratio of the methyl group absorbance intensity was 2:1, indicating the formation of a salt of carboxylic acid/amine=1:1. The equivalent molar ratio was also confirmed from the elemental analysis. The λmax of this salt in ethanol was 420 nm, which was changed to the low wavelength side by 20 nm when compared with that of the corresponding carboxylic acid (1). The melting point was 188° C. and the degree of the optical rotation $[\alpha]_D$ at Na-D ray in methanol was −5° (c=0.597). When the powder was irradiated by a 1.06μ light of Nd-YAG laser, the intensity of the second harmonic generation was about 3 times of that of m-nitroaniline.

Example 2

The carboxylic acid (12) prepared in the Synthesis Example 12 was used to form a salt with L-(−)-1-(phenyl)ethylamine in a THF solution in the same manner as in Example 1. The crystals were precipitated with the elapse of time. The resultant crystal was recrystallized from a mixed solvent of methanol/ethanol to obtain a pale yellow crystal having a melting point of 172° C.

The elemental analysis of the resultant crystal is C: 75.98%, H: 6.18%, and N: 8.06%, which was well coincided with the calculated value of C: 76.26%, H: 6.41%, and N: 8.09% in terms of a 1:1 salt of the carboxylic acid (12) and (phenyl)ethylamine.

IR spectrum showed broad carboxylate absorption at 2400–3200 $cm^{-1}$, and the absorption of COOH group at 1673 $cm^{-1}$ in the carboxylic acid (12) was shifted to about 1620 $cm^{-1}$ to reveal the formation of the salt.

The NMR spectrum gave an integrated intensity suggesting the formation of carboxylic acid/amine of 1:1. The degree of the optical rotation $[\alpha]_D$ at Na-D ray in methanol was +0.97 degree (c=0.597). The λmax in ethanol of the resultant salt was 355 nm, which was changed to the low wavelength side by 5 nm when compared with that of the corresponding carboxylic acid. When the powder was irradiated by a 1.06μ light of Nd-YAG laser, the intensity of the second harmonic generation was about 1.8 times of that of m-nitroaniline.

Examples 3-12

Optically active amine salts of various carboxylic acid compounds were obtained in the same manner as in Example 1, and their second harmonic generating abilities were determined. The results are shown in Table 2.

Examples 15-19

Various optically active amine salts were prepared in the same manner as in Example 14 and the second harmonic generating abilities were determined. The results are shown in Table 3.

TABLE 2

| Example No. | Carboxylic acid amine | m.p. (°C.) | Elemental analysis (Found/Calc.) | Degree of optical rotation $[\alpha]_D$ | $\lambda$max | SHG* generating ability |
|---|---|---|---|---|---|---|
| 3 | 11 PEA | 147 | C:74.92%, H:6.14%, N:8.77% (C:74.96%, H:6.30%, N:8.74%) | −2.01 | 325 nm | 1.2 |
| 4 | 2 PEA | 177 | C:70.69%, H:6.67%, N:12.37% (C:71.18%, H:6.88%, N:12.46%) | −0.33 | 385 nm | 0.4 |
| 5 | 9 PEA | 136 | C:69.96%, H:6.04%, N:8.61% (C:70.34%, H:6.23%, N:8.64%) | −0.88 | 320 nm | 0.3 |
| 6 | 10 PEA | 164 | C:72.82%, H:5.98%, N:9.58% (C:74.45%, H:6.26%, N:9.65%) | −0.73 | 288 nm | 0.1 |
| 7 | 13 PEA | 149 | C:70.41%, H:6.23%, N:8.62% (C:70.34%, H:6.23%, N:8.62%) | — | 285 nm | 0.3 |
| 8 | 5 PEA | 207 | C:67.74%, H:6.12%, N:7.94% (C:67.77%, H:6.27%, N:7.91%) | — | 333 nm | 0.2 |
| 9 | 4 PEA | 176 | C:67.79%, H:5.37%, N:8.21% (C:67.43%, H:5.37%, N:8.28%) | — | 337 nm | 0.3 |
| 10 | 8 PEA | 154 | C:63.31%, H:4.78?%, N:12.25% (C:63.70%, H:7.94%, N:12.38%) | +2.35 | 302 nm | 0.1 |
| 11 | 23 PEA | 175 | C:71.90%, H:5.64%, N:12.52% (C:72.04%, H:5.76%, N:12.61%) | — | 358 nm | 0.1 |
| 12 | 20 PEA | 150 | C:67.90%, H:5.64%, N:9.52% (C:67.58%, H:5.68%, N:9.85%) | — | 320 nm | 0.2 |

PEA: L-(−)-phenylethylamine
*(relative to m-nitroaniline (m-NA))

Example 13

A 0.67 g amount of the carboxylic acid 4 obtained in Synthesis Example 4 was dissolved in 7 ml of tetrahydrofuran, followed by adding 0.92 g of optically active R-(−)-1-(α-naphthyl)ethylamine. The resultant solid was filtered and recrystallized from ethanol. The melting point was 171° C. and the ratio of the integrated intensity of the absorption peaks of the carboxylic acid (4) component to (α-naphthyl)ethylamine component such as methyl group obtained from the NMR spectrum was 1:1.

The elemental analysis was C 71.55%, H 5.20%, N 7.21%, which was coincided with the calculated value, C 71.55%, H 5.26%, N 7.20% which was based upon the formation of a 1:1 salt of the carboxylic acid and the amine.

When the resultant crystal was finely powdered and the generation of the second harmonic generation was determined, the intensity of the emission is about 1.5 times of that of the urea.

Example 14

A 0.93 g amount of the carboxylic acid (1) obtained in Synthesis Example 1 was dissolved in 10 ml of tetrahydrofuran, followed by adding 0.70 g of S-(−)-1-(α-naphthyl) ethylamine thereto. The resultant solid was recovered and washed thoroughly with tetrahydrofuran. After drying, the crystal having a melting point of 171° C. The degree $[\alpha]_D$ of the optical rotation of the sample in methanol was −30.0 degree (c=0.04) and λmax was 421 nm. The maximum wave length was approximately coincide with that of Example 1. The second harmonic generation generating ability of the crystal was about 3.9 times of that of urea. Furthermore, when the crystalline powder was exposed to the laser beam for a long time, apparent damage was not observed.

TABLE 3

| Example | Carboxylic acid | Optically active amine | SHG generating ability *1 |
|---|---|---|---|
| 15 | Synthesis Example 5 | 1-Phenyl-2-methylethylamine | 1.5 |
| 16 | Synthesis Example 7 | 1-(Phenyl)ethylamine | 5.0 |
| 17 | Synthesis Example 7 | 1-(α-naphthyl)ethylamine | 3.5 |
| 18 | Synthesis Example 5 | 1-(Phenyl)ethylamine | 2.0 |
| 19 | Synthesis Example 5 | 1-Phenyl-2-aminopropane | 2.5 |

*1 Based on urea powder

Example 20

A 1.54 g amount of the thiophene-containing carboxylic acid (17) obtained in Synthesis Example 17 was dissolved in 40 ml of tetrahydrofuran, followed by adding 1.46 g of optically active R-(−)-1-(phenyl)ethylamine. The precipitated solid was recovered and recrystallized from ethanol to obtain the crystal having a melting point of 171° C. (decomposition).

The elemental analysis values were C 63.85%, H 5.15%, N 9.30%, S 10.40%, which were well coincide with the calculated values, C 63.97%, H 5.38%, N 9.33%, S 10.17% based upon a 1:1 amine salt of the carboxylic acid. The integrated intensity ratio of the absorption peak of the carboxylic acid of Synthesis Example 17 and phenethylamine from the NMR spectrum. The maximum absorption wavelength was 322 nm. When the second harmonic generation was determined after the crystal was finely powdered, the green emission having the ability of about twice of that of urea was observed.

Example 21

A 1.51 g amount of the 3-substituted thiophene carboxylic acid (18) obtained in Synthesis Example 18 was dissolved in 20 ml of tetrahydrofuran, followed by adding 1.20 g of R-(−)-1-(phenyl)ethylamine. The precipitated solid was recovered and recrystallized from ethanol, after drying, to obtain the crystal having a melting point of 171° C. (decomposition).

The elemental analysis values were C 63.82%, H 5.07%, N: 9.31%, S 10.57%, which were well coincide with the calculated values, C 63.97%, H 5.38%, N 9.33%, S 10.17% based upon a 1:1 amine salt of the carboxylic acid. The integrated intensity ratio of the absorption peak of the carboxylic acid of Synthesis Example 18 and phenethylamine from the NMR spectrum. The maximum absorption wavelength was 322 nm. The second harmonic generating ability of the crystal was 3 times of that of urea and the maximum absorption wavelength of the sample in ethanol was 322 nm.

Example 22

A 0.99 g amount of the carboxylic acid (21) obtained in Synthesis Example 21 was dissolved in 40 ml of tetrahydrofuran, followed by adding 0.78 g of optical active R-(−)-1-(phenyl)ethylamine thereto.

After n-hexane was then added, the precipitated solid was recovered. The solid was recrystallized from ethanol to obtain the crystal having a melting point of 121° C. (decomposition). The elemental analysis data were C 69.55%, H 5.95%, and N 9.00%, which was well coincided with the calculated values of the optically active amine salt of the synthesized carboxylic acid (21). The emission having an intensity of about 5 times of that of urea was observed by an Nd-YAG laser beam. The maximum absorption wavelength of the sample in ethanol was 350 nm.

Example 23

A 3.20 g amount of the carboxylic acid (12) obtained in Synthesis Example 12 was dissolved in 50 ml of tetrahydrofuran, followed by adding 2.50 g of R-(−)-2-amino-1-butanol thereto.

The precipitation was momentarily generated and, after filtering, 3.00 g of yellow solid was recovered a mixed solvent of ethanol/methanol to obtain 2.1 g of the needle having a melting point of 187° C. The optical rotation degree in methanol with an Na-D ray was 16 degree. The maximum absorption of the sample in methanol was 355 nm amine salt of the synthesized carboxylic. The second harmonic generating ability of the powder was 33 times of that of urea.

Examples 24–42

The salts of various carboxylic acids and optically active alcohol amines were carried out in the same manner as in Example 23 and the second harmonic generating abilities of the resultant crystals were determined.

The results are shown in Table 4.

TABLE 4

| Example | Carboxylic acid | Optically active amine base | SHG generating ability *1 |
|---|---|---|---|
| 24 | 23 | 1-Amino-2-propanol | |
| 25 | 1 | 2-Amino-1-butanol | 6.9 |
| 26 | 2 | 2-Amino-1-butanol | 1.8 |
| 27 | 10 | 2-Amino-1-butanol | 1.2 |
| 28 | 2 | 1-Amino-2-propanol | 30.0 |
| 29 | 10 | 1-Amino-2-propanol | 1.1 |
| 30 | 1 | 1-Amino-2-propanol | 26.0 |
| 31 | 12 | 1-Amino-2-propanol | 1.1 |
| 32 | 2 | 2-Amino-1-propanol | 0.5 |
| 33 | 10 | 2-Amino-1-propanol | 0.2 |
| 34 | 12 | 2-Amino-1-(p-nitrophenyl)-1,3-propane diol | 0.7 |
| 35 | 12 | 2-Dimethylamino-1-phenyl-1-phenyl-1-benzyl-1-propanol | 0.6 |
| 36 | 17 | 2-Amino-1-butanol | 3.0 |
| 37 | 17 | 2-Amino-1-propanol | 1.5 |
| 38 | 4 | 2-Amino-1-propanol | 1.3 |
| 39 | 20 | 2-Amino-1-propanol | 3.8 |
| 40 | 20 | 2-Amino-1-butanol | 5.0 |
| 41 | 21 | 2-Amino-1-butanol | 3.6 |
| 42 | 19 | 2-Amino-1-butanol | 3.2 |

*1 Based upon urea powder

Example 43

A 0.89 g amount of dimethoxy substituted conjugated carboxylic acid (7) obtained in Synthesis Example 7 was dissolved in 10 ml of THF, followed by adding 0.42 g of dextrorotatory R-(−)-2-amino-1-butanol. The resultant precipitates was filtered and recrystallized from ethanol to obtain the white crystal having a melting point of 130.5° C. The NMR spectrum of the resultant solid revealed the integrated intensity, which shows the formation of 1:1 by mole salt of the corresponding carboxylic acid and amine. The crystal was finely powdered and the second harmonic generating ability was determined. As a result, the emission capability thereof was 5.8 times of that of urea. The maximum absorption of the sample in ethanol was 370 nm. The powder of 2-methyl-4-nitroaniline used as a control was melted and carbonized under the determination conditions of the second harmonic generating ability, whereas the change in the emission capability of the present sample with the elapse of time was not observed and the damage resistance of the present sample against light was good.

Example 44

The amine salt was formed in the same manner as in Example 43, except that R-(−)-1-amino-2-propanol was used as the optically active amine. The second harmonic generating ability of the resultant salt was about 4 times of that of urea and the ability was not changed with the elapse of time. Thus, it has been observed that a high resistance to the light damage was good.

Example 45

The salt was formed in the same manner as in Example 43, except that the dimethoxy compound (5) obtained in Synthetic Example 5 as the carboxylic acid. The emission capability of the resultant salt was not changed when the sample was exposed to a laser beam for a long time.

Example 46

A 2.30 g amount of L-phenylalanine ethyl ester hydrochloride was suspended in 50 ml of ether, followed by adding thereto 0.96 g of triethyl amine and further 30 ml of water, ten ml of the supernatant ether phase was recovered and this solution was added to a previously prepared solution of 0.26 g of the above-mentioned carboxylic acid (1) in 6 ml of THF. The needles were obtained with the elapse of time. The decomposition of this crystal was 180° C. When the second harmonic generating ability of this crystal was determined, the intensity was about 15 times of that of urea.

Example 47

A 3.30 g amount of L-valine methyl ester hydrochloride was suspended in 50 ml of ether, followed by adding thereto 1.89 g of triethyl amine to obtain an ether solution of the L-valine methyl ester. This solution was added to a solution of 0.12 g of the above-mentioned carboxylic acid (2) in 10 ml of THF to obtain the needles. When the second harmonic generating ability of the crystal powder was determined, the intensity was 3 times of that of urea.

Examples 48-64

The amine salts of α-amino acid esters of various carboxylic acids were obtained in the same manner as in Examples 1 and 2 and the second harmonic generating abilities were determined.

The results are shown in Table 5.

TABLE 5

| Example | Carboxylic acid | Optically active amine base | SHG generating ability *1 |
|---|---|---|---|
| 48 | 10 | L-Phenylalanine ethyl ester | 16 |
| 49 | 12 | L-Phenylalanine ethyl ester | 10 |
| 50 | 8 | L-Phenylalanine ethyl ester | 5 |
| 51 | 10 | L-Phenylalanine ethyl ester | 7 |
| 52 | 13 | L-Phenylalanine ethyl ester | 5 |
| 53 | 15 | L-Phenylalanine ethyl ester | 4 |
| 54 | 19 | L-Phenylalanine ethyl ester | 4 |
| 55 | 1 | L-Valine methyl ester | 12 |
| 56 | 11 | L-Valine methyl ester | 15 |
| 57 | 14 | L-Valine methyl ester | 4 |
| 58 | 12 | L-Valine methyl ester | 18 |
| 59 | 16 | L-Valine methyl ester | 3 |
| 60 | 1 | D-Phenylglycine methyl ester | 10 |
| 61 | 9 | D-Phenylglycine methyl ester | 5 |
| 62 | 7 |  | 11 |
| 63 | 1 | α-N-Benzoyl-L-alginine ethyl ester | 8 |
| 64 | 7 | α-N-Benzoyl-L-alginine ethyl ester | 3 |

*1 Based on urea

Example 65

Synthesis of S-(−)-phenethyl 2-cyano-5-phenyl-2,4-pentadienocarboxamide (24)

A 3.3 g amount of an acid chloride of the compound (11) obtained by thermally treating the compound (11) with thionyl chloride was added, under vigorous stirring, to 20 ml of dioxane containing 1.8 g of S-(−)-phenethyl amine and 1.5 g of triethyl amine. After stirring at room temperature for further 3 hours, the reaction product was added to a large amount of water and the resultant precipitates were filtered, followed by recrystallizing to obtain 2.7 g of yellow needles having a melting point of 117° C.

Elemental analysis: C 79.50%, H 6.05%, N 9.30% (Calc. C 79.44%, H 6.00%, N 9.26%).

IR absorption spectrum: —NH— group at 3364 $cm^{-1}$, CN group at 2216 $cm^{-1}$, amine I, II at 1649 $cm^{-1}$ and 1522 $cm^{-1}$.

λmax in dioxane: 336 nm.

When the second harmonic generating ability of the crystal was determined, the intensity was about 11 times of urea and there are no substantial deformation, when the sample was irradiated for a long time.

Example 66

Synthesis of S-(−)-phenethyl 2-cyano-7-phenyl-2,4,6-hepta-triene-1-carboxamide (25)

A 1.79 g amount of the acid chloride of the compound (11) (m.p. 143° C.) obtained by thermally treating the compound (11) with thionyl chloride was added, under vigorous stirring, to 30 ml of THF containing 1.06 g of S-(−)-phenethyl amine and 0.70 g of pyridine dissolved therein. After completion of the reaction, a large amount of water was added to the reaction product and the resultant precipitates were filtered, followed by recrystallizing, to obtain 1.6 g of a crystal having a melting point of 128° C.

Elemental analysis: C 80.74%, H 6.20%, N 8.66% (Calc. C 80.44%, H 6.15%, N 8.53%).

IR absorption spectrum: —NH— group at 3360 $cm^{-1}$, —CN group at 2216 $cm^{-1}$, presence of amine I, II at 1649 $cm^{-1}$ and 1522 $cm^{-1}$.

λmax in ethanol: 370 nm.

NMR spectrum: the methyl group of phenethyl group at 1.57 ppm, —CH= at 7.99 ppm, 6.79-7.05 ppm, 6.82 ppm (Thus, the structure of the desired compound was confirmed).

When the second harmonic generating ability of the crystal was determined, it was observed that the intensity was 1.1 times of urea and there are no substantial deformation after a long time irradiation of a laser beam.

Example 67

Synthesis of S-(−)1-(α-naphthyl)ethyl 2-cyano-7-phenyl-2,4,6-hepta-triene-1-carboxamide (26)

To a dry THF solution of an equivalent mixture of the compound (12) and S-(−)-1-(α-naphthyl)ethylamine, dicyclohexylcarbo diimide was added, followed by stirring for one night. The precipitated dicyclohexyl urea was recovered by filtration and the mother liquor was concentrated, followed by recrystallizing from a mixture of ethanol/methanol to obtain a white solid having a melting point of 100° C.

IR absorption spectrum: —NH— group at 3360 $cm^{-1}$, CN group of 2220 $cm^{-1}$, presence of amide I, II at 1650 $cm^{-1}$ and 1522 $cm^{-1}$.

When the second harmonic generating ability of the crystal was determined, the intensity was 4 times of that of urea and there are no substantial deformation after a long time irradiation of a laser beam.

Examples 68-72

Various optically active amides shown in Table 6 were obtained from various carboxylic acid and optically active acid amide.

TABLE 6

| Example No. | Optically Active Acid Amide Carboxylic acid component | Amine component | Synthesis method | m.p. (°C.) | SHG |
|---|---|---|---|---|---|
| 68 | p-NO$_2$—C$_6$H$_4$—CH=C(CN)COOH | PRO | DCC | 135 | W |
| 69 | p-CH$_3$—O—C$_6$H$_4$—CH=C(CN)COOH | S-(—)PEA | CL | 126 | S |
| 70 | H—C$_6$H$_4$—CH=C(CN)COOH | R-(—)sBA | CL | 98 | W |
| 71 | p-CH$_3$—O—C$_6$H$_4$—CH=CH—CH=C(CN)COOH | R-(—)sBA | CL | 140 | S |
| 72 | C$_6$H$_5$—CH=CH—CH=CH—CH=C(CN)COOH | S-(—)PEA | DCC | 158 | S |

PRO: L-prolinol
S-(—)PEA: S-(—)-phenethylamine
R-(—)sBA: R-(—)-2-amino-1-butanol
DCC: Dicyclohexyl carbodiimide method (Example 67)
CL: Acid chloride method (Example 66)
W: Weak emission
S: Strong emission

We claim:

1. An organic nonlinear optical crystal of a substance having the formula (I):

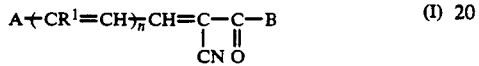
(I)

wherein
R$^1$ represents —H or —CH$_3$;
n is 0, 1, or 2;
A represents Z$^1$—Ar—,

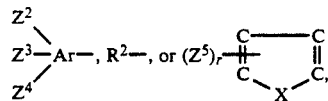

wherein Ar represents a 6–14 membered aromatic group including a heterocyclic ring or bisphenylene type ring;
Z$^1$ represents H—, R$^5$R$^6$N—, R$^7$O—, R$^8$S—, NC—, R$^9$OCO—, R$^{10}$COO—, O$_2$N—, R$^{11}$R$^{12}$NOC—, R$^{13}$CO(R$^{14}$)N—, or R$^{15}$—;
Z$^2$, Z$^3$, and Z$^4$ independently represent H—, a C$_1$–C$_8$ alkyl, R$^{16}$O—, R$^{17}$R$^{18}$N—, R$^{19}$S—, or O$_2$N—, with the proviso that Z$^2$ and Z$^3$ together may form —O—CH(R$^{20}$)—O—;
R$^2$ represents H— or a C$_1$–C$_{12}$ alkyl;
R$^5$ to R$^{20}$ independently represent H—, or a C$_1$–C$_{10}$ hydrocarbon residue;
Z$^5$ independently represents H—, a C$_1$–C$_8$ saturated hydrocarbon residue, O$_2$N—, R$^{21}$O—, R$^{22}$S—, NC— or R$^{23}$R$^{24}$N—, wherein R$^{21}$ to R$^{24}$ independently represent H or a C$_1$–C$_8$ saturated hydrocarbon residue;
X represents —S—, —O—, or >NR$^{28}$;
r is 0 or an integer of 1 to 3; and
R$^{28}$ represents H or a hydrocarbon group having 1 to 8 carbon atoms;
B represents —OH.Amine* where Amine* represents an optically active amine selected from the group consisting of 1-(phenyl)ethylamine, 1-(α-naphthyl)ethylamine, 1-phenyl-2-(methyl)ethylamine, 1-phenyl-2-aminopropane, brucine, 2-amino-1-butanol, 1-amino-2-propanol, 2-amino-1-propanol, 2-amino-1-(p-nitrophenyl)-1,3-propanediol, 2-dimethyl-amino-1-phenyl-1-benzyl-1-propanol, 1-(N,N-dimethyl-amino)-1-phenyl-propylamine, and a residue of an optically active α-amino acid and the derivative thereof; —NR$^4$Y where R$^4$ represents —H or a single bond; Y represents —(CH$_2$)$_p$—CO$^1$O$^2$O$^3$ where p is 0 or 1; Q$^1$, Q$^2$, and Q$^3$ are different and represent —H, a C$_1$–C$_5$ alkyl, phenyl, naphthyl, —OH, —CH$_2$OH, —COOR$^{25}$, —CNR$^{26}$R$^{27}$, a residue of an α-amino acid from which an amino group is removed, where R$^{25}$ to R$^{27}$ independently represent —H or —C$_1$–C$_8$ hydrocarbon residue; or —CQ$^4$Q$^5$Q$^6$ where Q$^4$, Q$^5$ and Q$^6$ are different and Q$^4$ and Q$^5$ are as defined for Q$^1$, Q$^2$ and Q$^3$ and Q$^6$ represents —CH$_2$)$_q$ or which one bond is linked to the bond of R$^4$ where q is an integer of 1 to 4.

2. An organic nonlinear optical substance as claimed in claim 1, wherein in the formula (I), R$^1$ represents H—, Z$^1$ represents H—, R$^5$R$^6$N—, R$^7$O—, R$^8$S, NC—, R$^9$OCO—, R$^{10}$COO—, O$_2$N—, R$^{11}$R$^{12}$NOC—, R$^{13}$CO(R$^{14}$)N—, or R$^{15}$—, Ar represents an aromatic group having 5 to 14 carbon atoms, and B represents —OH.Amino*wherein Amine* represents an optically active amine selected from the group consisting of 1-(phenyl)ethylamine, 1-(α-naphthyl)ethylamine, 1-(phenyl)-2-(methyl)ethylamine, 1-phenyl-2-aminopropane, and brucine.

3. An organic nonlinear optical substance as claimed in claim 1, wherein, in the formula (I), R$^1$ represents H, Z$^1$ represents H—, R$^5$R$^6$N—, R$^7$O—, R$^8$S—, NC—, O$_2$N—, R$^9$OCO—, R$^{11}$R$^{12}$NOC—, R$^{13}$CO(R$^{14}$)N—, or R$^{15}$—, Ar represents an aromatic group having 6 to 14 carbon atoms, and B represents —OH.Amine* wherein Amine*represents an optically active amine selected from the group consisting of 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino)-1-phenyl-propylamine.

4. An organic nonlinear optical substance as claimed in claim 1, wherein, in the formula (I), R$^1$ represents H, A represents

wherein one of Z$^2$, Z$^3$, and Z$^4$ represents H and the remainder independently represents C$_1$–C$_{10}$alkyl, R$^{16}$O—, R$^{17}$R$^{18}$N—, R$^{19}$S—, or O$_2$N—, Ar represents an aromatic group having 6 to 14 carbon atoms, and B represents a residue of an optically active amine selected from the group consisting of 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, and 1-(N,N-dimethylamino)-1-phenylpropylamine.

5. An organic nonlinear optical substance as claimed in claim 1, wherein, in the formula (I), $R^1$ represents H, A represents

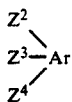

wherein one of $Z^2$, $Z^3$ and $Z^4$ represents H— and the remainder independently represents $C_1$–$C_{10}$alkyl, $R^{16}O$—, $R^{17}R^{18}N$—, $R^{19}S$—, or $O_2N$—, Ar represents an aromatic group having 6 to 14 carbon atoms, and B represents a residue of an optically active amine selected from the group consisting of 1-(phenyl)ethylamine, 1-(α-naphthyl)ethylamine, 1-phenyl-2-(methyl)ethylamine, 1-phenyl-2-aminopropane, and brucine.

6. An organic nonlinear optical substance as claimed in claim 1, wherein, in the formula (I), $R^1$ represents H—, A represents $Z^1$Ar—, $Z^1$ represents H—, $R^5R^6N$—, $R^7O$—, $R^8S$—, NC—, $O_2N$—, $R^9OCO$—, $R^{10}COO$—, $R^{11}R^{12}NOC$—, $R^{13}CO(R^{14})N$—, or $R^{15}$—, Ar represents an aromatic ring having 6 to 14 carbon atoms, and B represents —$NR^4Y$.

7. An organic nonlinear optical substance as claimed in claim 1, wherein, in the formula (I), $R^1$ represents H—; A represents $Z^1$—Ar—, $Z^1$ represents $R^5R^6N$—, $R^7O$—, $R^8S$—, NC—, $R^9OCO$—, $R^{10}COO$—, $R^{11}R^{12}NOC$—, $R^{13}CO(R^{14})N$—, or $R^{15}$ Ar represents an aromatic group having 6 to 14 carbon atoms, and B represents —OH.Amine* wherein Amine* represents an optically active α-amino acid or the derivative thereof.

8. An organic nonlinear optical substance as claimed in claim 1, wherein, in the formula (I), $R^1$ represents H—, A represents

where one of $Z^2$, $Z^3$, and $Z^4$ represents H or substituted $C_1$–$C_8$ alkyl, the remainder of $Z^2$, $Z^3$, and $Z^4$ represents together methylene dioxy group wherein the dioxy groups are bonded to the adjacent positions of Ar, Ar represents an aromatic group having 6 to 14 carbon atoms, and B represents —OH.Amine* wherein Amine* represents an optically active amine selected from the group consisting of 1-(phenyl)ethylamine, -(α-naphthyl)ethylamine, 1-phenyl-2-(methyl)ethylamine, -phenyl-2-aminopropane, brucine, 2-amino-1-butanol, -amino-2-propanol, 2-amino-1-propanol, 2-amino-1-(p-nitrophenyl)-1,3-propanediol, 2-dimethylamino-1-phenyl-1-benzyl-1-propanol, 1-(N,N-dimethylamino)-1-phenyl-propylamine, and a residue of an optically active α-amino acid and the derivative thereof; or —$NR^4Y$.

9. An organic nonlinear optical substance as claimed in claim 1, wherein, in the formula (I), $R^1$ represents H or $CH_3$, A represents $R^2$ where $R^2$ represents H or an alkyl group having 1 to 12 carbon atoms, and B represents —OH Amine* wherein Amine* represents an optically active amine selected from the group consisting of 1-(phenyl)ethylamine, 1-(α-naphthyl)ethylamine, 1-phenyl-2-methylethylamine, 1-phenyl-2-aminopropane, brucine, 2-amino-1-butanol, 1-amino-2-propanol, 2-amino-1-propanol, 2-amino-1-(p-nitrophenyl)-1,3-propanediol, 2-dimethylamino-1-phenyl-1-benzyl-1-propanol, 1-(N,N-dimethylamino)-1-phenyl-1-benzyl-1-propanol, 1-(N,N-dimethylamino)-1-phenyl-propylamine, and a residue of an optically active α-amino acid and the derivative thereof.

10. An organic nonlinear optical substance as claimed in claim 1, wherein, in the formula (I), $R^1$ represents H, A represents

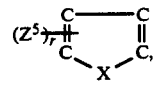

and B represents —OH.Amine* wherein Amine* represents an optically active amine selected from the group consisting of 1-phenylethylamine, 1-α-naphthylamine, -phenyl-2-methylethylamine, 1-phenyl-2-aminopropane, brucine, 2-amino-1-butanol, 1-amino-2-propanol, -amino-1-propanol, 2-aminol-(p-nitrophenyl)-1,3-propanediol, 2-dimethylamino-1-phenyl-1-benzyl-1-propanol, 1-(N,N-dimethylamino)-1-phenyl-propylamine, and a residue of an optically active α-amino acid and the derivatives thereof; or —$NR^4Y$.

11. An organic nonlinear optical substance as claimed in 1, wherein, in the formula (I), $R^1$ represents H, A represents

wherein one of $Z^2$, $Z^3$, and $Z^4$ represents H— and the remainder independently represents $C_1$–$C_{10}$alkyl, $R^{16}O$—, $R^{17}R^{18}N$—, or $O_2N$—, Ar represents an aromatic group having 6 to 14 carbon atoms, and B represents —OH.Amine* wherein Amine* represents an optically active α-amino acids or the derivatives thereof.

* * * * *